US00PP28874P3

(12) United States Plant Patent
White

(10) Patent No.: US PP28,874 P3
(45) Date of Patent: Jan. 16, 2018

(54) PEAR TREE NAMED 'PREMP027'

(50) Latin Name: ***Pyrus bretschneideri*×*Pyrus communis***
Varietal Denomination: PremP027

(71) Applicant: Allan G. White, Havelock North (NZ)

(72) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 14/544,401

(22) Filed: Dec. 31, 2014

(65) Prior Publication Data

US 2015/0195970 P1 Jul. 9, 2015

Related U.S. Application Data

(60) Provisional application No. 61/924,158, filed on Jan. 6, 2014.

(51) Int. Cl.
*A01H 5/08* (2006.01)

(52) U.S. Cl.
USPC ..... Plt./176

(58) Field of Classification Search
USPC ..... Plt./176
See application file for complete search history.

*Primary Examiner* — Keith O Robinson
(74) *Attorney, Agent, or Firm* — Michelle Bos Legal LLC

(57) ABSTRACT

A new and distinct pear tree named 'PremP027' is disclosed. The new pear is notable for its attractive appearance, superb texture, improved flavor and long shelf life.

1 Drawing Sheet

Latin name of the genus and species of the plant claimed: *Pyrus bretschneideri*×*Pyrus communis*.

Variety denomination: 'PremP027'.

BRIEF DESCRIPTION OF THE PHOTOGRAPHS

FIG. 1 shows the fruit of a 'PremP027' pear tree at harvest time.

BRIEF DESCRIPTION OF THE VARIETY

The new variety of pear tree 'PremP027' was created in the course of a planned breeding program carried out at Motueka, New Zealand. 'PremP027' originated as a result of a controlled cross of 'Max Red Bartlett' (seed parent, U.S. Plant Pat. No. 741) and 'Snowflake' (pollen parent, not patented) in 1989. 'PremP027' was selected in 1996 as a single plant from among a population of seedlings derived from the parents, and was selected for its quality of fruit. It is distinguished from its parents by its shape and color. 'Max Red Bartlett' fruit is pyriform in shape with high coverage of red skin color compared to 'PremP027' which has no red skin color. 'PremP027' is almost round with slight tapering at the stem and calyx end. Fruit of 'PremP027' ripens 7-10 days later than 'Max Red Bartlett'. Fruit of 'PremP027' has less prominent lenticels than 'Snowflake' and ripens approximately 14-21 days earlier. 'PremP027' is also distinguishable from other known varieties, such as 'Nijisseiki' (U.S. Plant Pat. No. 8,529). 'Nijisseiki' has more round fruit than 'PremP027' and ripens approximately 7-10 days earlier. 'PremP027' is distinguishable from related variety 'PremP003' (U.S. Ser. No. 14/544,403, pending) by its more upright growth habit and early harvest maturity. 'PremP027' is ready for harvest about three weeks earlier than 'PremP003'.

Asexual propagation by budding was first carried out in Motueka and Havelock North, New Zealand. The variety has since been observed over a number of asexually propagated generations, and has been found to remain true to type.

DETAILED BOTANICAL DESCRIPTION OF THE VARIETY

The following detailed botanical description is based on observations made during the 2013 growing season at Parker, Wash. on 5 year old trees. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Vigor*.—Medium.
*Habit*.—Upright.
*Branching*.—Medium.
*Size*.—Height 10 feet; Spread 5 feet.
*Trunk*.—Diameter at graft union 10.2 cm.
*Bark texture*.—Smooth.

Branch:

*Size*.—Diameter 3.5 cm at 86 cm above ground.
*Crotch angle relative to trunk*.—70°.
*Bark texture*.—Smooth.

Dormant one-year-old shoot:

*Size*.—Diameter 1.7 cm, length 86 cm.
*Color*.—146B.
*Internode length*.—6 to 8 cm.
*Lenticels*.—Quantity 10 per square inch, color white 155B, diameter 0.05 cm.
*Vegetative bud*.—Acute, slightly held out.
*Bark texture*.—Smooth.

Growing young shoot:
*Anthocyanin coloration of growing tip.*—Medium.
*Pubescence of upper third of shoot.*—Weak.
Flower buds:
*Length.*—2.3 cm.
*Diameter.*—0.7 cm.
*Color.*—White N155A with pink 62A stripe.
Flowers:
*Petals.*—5 per flower, margins touching.
*Petal size.*—Length 2.5 cm, diameter 2.0 cm.
*Petal shape.*—Rounded.
*Petal color.*—White N155A.
*Petal texture.*—Smooth upper and lower surface.
*Sepals.*—2, length 1 cm, diameter 0.1 cm.
*Pedicel.*—Length 5.5 cm, diameter 0.2 cm, color yellow-green 145A.
*Anthers.*—Length 0.1 cm, 20 per flower.
*Pollen.*—Present, color yellow 2C.
*Stigma.*—Length 0.1 cm, color yellow-green 154D.
*Ovary.*—Length 0.3 cm, color yellow-green 144C.
*Style.*—Length 0.7 cm, color yellow-green 154D.
*Bloom period.*—First bloom April 12, full bloom April 18 in Parker, Wash.
Leaf:
*Attitude in relation to shoot.*—Upward.
*Blade margin.*—Serrulate.
*Size.*—Length 8.5 cm, width 7 cm.
*Shape.*—Ovate with rounded base, acuminate tip.
*Upper surface.*—Color yellow-green 146D, texture smooth.
*Lower surface.*—Color yellow-green 145C, texture smooth with raised veins.
Petiole:
*Length.*—5 cm.
*Diameter.*—0.1 cm.
*Color.*—Yellow-green 145C. Stipules present.

Fruit:
*Size.*—Diameter 9.6 cm, length 15 cm.
*Position of maximum diameter.*—Middle.
*Profile of sides.*—Convex.
*Ribbing.*—Absent.
*Size of eye.*—2 cm.
*Depth of eye basin.*—0.5 cm.
*Width of eye basin.*—1 cm.
*Relief of area around eye.*—smooth.
*Stalk.*—Length 4.5 cm, width at limb attachment 0.5 cm, color greyed-orange 176D and yellow-green 154C.
*Depth of stalk cavity.*—0.25 cm.
*Attitude of stalk in relation to fruit.*—Oblique.
*Width of stalk cavity.*—1 cm.
*Size of lenticels.*—0.1 cm.
*Color of lenticels.*—Brown 200D.
*Ground color of skin.*—Yellow-green 154C.
*Overcolor.*—Absent.
*Quantity per cluster.*—2 to 3; Flesh is very crisp and very juicy.
*Flesh color.*—White 155B.
*Quantity of seeds.*—10.
*Seed size.*—Width 0.5 cm, length 1 cm.
*Seed shape.*—Ovate.
*Seed color.*—Black 200A.
*Harvest date.*—Early season (mid- to late August).
Disease resistance/susceptibility: None noted.
Storage: Excellent storage performance of at least 3 months.
Use: Fresh Market.

The invention claimed is:

1. I claim a new and distinct pear tree substantially as shown and described herein.

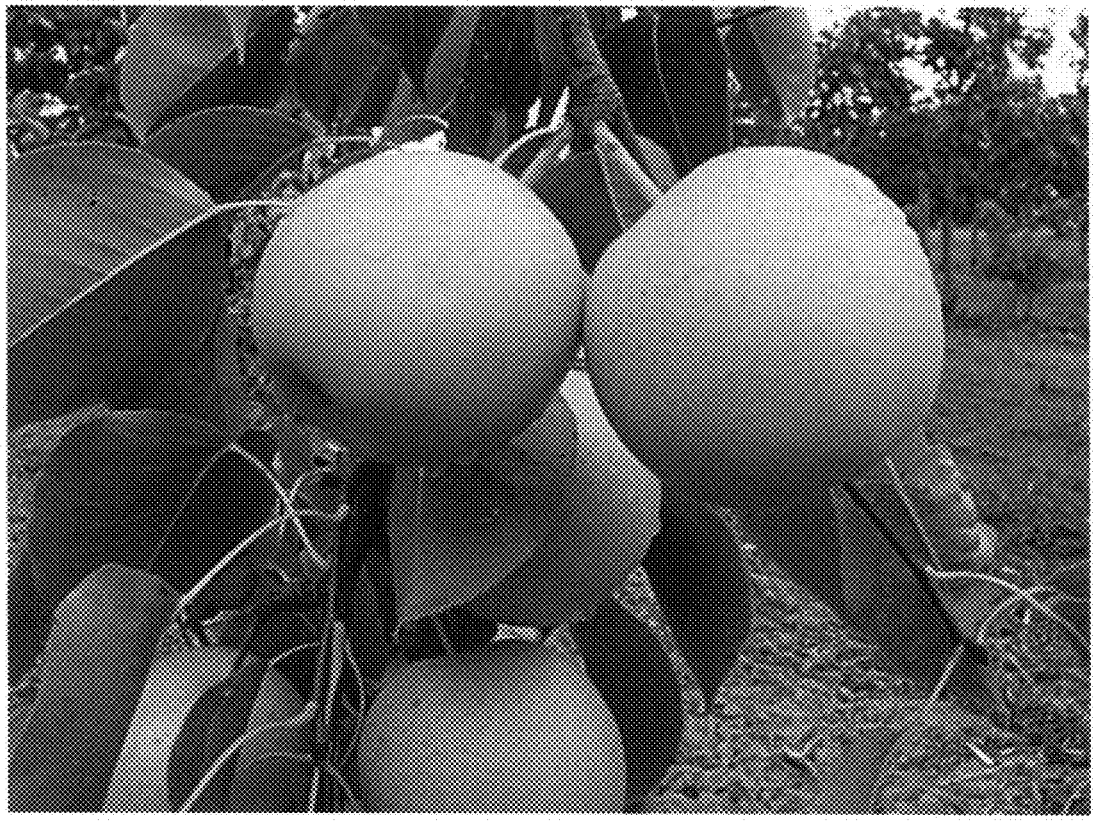

* * * * *